United States Patent
Ueno

[11] Patent Number: 5,872,614
[45] Date of Patent: Feb. 16, 1999

[54] EYE REFRACTIVE POWER MEASUREMENT APPARATUS

[75] Inventor: Yasunori Ueno, Kawasaki, Japan

[73] Assignee: Nikon Corporation, Tokyo, Japan

[21] Appl. No.: 848,256

[22] Filed: Apr. 29, 1997

[30] Foreign Application Priority Data

Apr. 30, 1996 [JP] Japan .................................. 8-132693

[51] Int. Cl.$^6$ .................................................. A61B 3/10
[52] U.S. Cl. ........................................ 351/211; 351/205
[58] Field of Search .................................... 351/205, 206, 351/208, 211, 216, 222, 237, 239

[56] References Cited

U.S. PATENT DOCUMENTS

| | | | |
|---|---|---|---|
| 5,355,253 | 10/1994 | Nanjo et al. | 351/216 |
| 5,371,558 | 12/1994 | Kohayakawa | 351/211 |
| 5,483,305 | 1/1996 | Kohayakwa | 351/243 |

FOREIGN PATENT DOCUMENTS

| | | | |
|---|---|---|---|
| 5220112 | 8/1993 | Japan | A61B 3/103 |
| 788081 | 4/1995 | Japan | A61B 3/10 |

*Primary Examiner*—Huy Mai
*Attorney, Agent, or Firm*—Chapman and Cutler

[57] ABSTRACT

A type of eye refractive power measurement apparatus is capable of measuring the refractive power of left and right eyes through a common measurement optical system and without movement of the entire apparatus. The measurement apparatus includes a measurement system in which a beam of light is projected on the fundus of an eye under examination. The light reflected from the fundus of the eye is received by a light-receiving element. Based on the photoelectric output of the light-receiving element, the refractive power of the eye being examined is measured. A left eye/right eye switching prism selectively guides the light from the measurement system to one of the eyes which is to be subjected to examination. The light is also guided by the switching prism from the selected eye to the measurement system.

12 Claims, 3 Drawing Sheets

EYE REFRACTIVE POWER MEASUREMENT APPARATUS

BACKGROUND OF THE INVENTION

1. Field of the Invention

This invention pertains to a type of eye refractive power measurement apparatus used for measurement of the refractive power of a patient's eyes during an examination.

2. Description of Related Art

Conventionally, when the refractive powers of left and right eyes of a patient are to be measured, the refractive power of one of the eyes is initially measured. The entire eye refractive power measurement apparatus is then moved so as to measure the refractive power of the other eye. In another conventional procedure, the refractive powers of the left and right eyes of the patient are separately measured using an apparatus having one optical system for the right eye and another optical system for the left eye.

In the first conventional eye refractive power measurement procedure mentioned above, in which the refractive powers of both eyes are measured by moving an entire measuring apparatus, a sliding table is needed to move the apparatus. When measuring the refractive power of an eye, the position of the apparatus must be matched with respect to and aligned with the eye under examination. This is a disadvantage.

In the second conventional eye refractive power measurement procedure mentioned above, in which a first optical system is used for obtaining measurements from the right eye and a second optical system is used for obtaining measurements from the left eye, two independent measurement optical systems are contained in the measuring apparatus. As a result, the size of the apparatus becomes larger and the cost increases. This is undesirable.

SUMMARY OF THE INVENTION

The object of this invention is to solve the problems of the conventional arrangements mentioned above by providing a type of eye refractive power measurement apparatus that is capable of measuring the refractive powers of left and right eyes through a common measurement optical system without moving the entire apparatus.

The eye refractive power measurement apparatus includes a measurement system in which a beam of light is projected on the fundus of the eye under examination. The light reflected from the fundus of the eye under examination is received by a light-receiving element and, based on the photoelectric output of the light-receiving element, the refractive power of the eye under examination is measured. In the measurement apparatus, a left eye/right eye switching element selectively guides the light from the measurement system to one of the eyes under examination and from the selected eye back to the measurement system.

The left eye/right eye switching element preferably has a first reflecting surface and a second reflecting surface. The element can move between a first position, in which the light from the measurement system is reflected by the first reflecting surface and guided toward one of the eyes for examination, and a second position, in which the light from the measurement system is reflected by the second reflecting surface and guided to the other eye for examination.

The invention also preferably has a pupil distance adjusting device placed between the left eye/right eye switching element and at least one of the eyes being examined. Parallel movement of the light from the measurement system is conducted. The center of the particular eye under examination, which differs from that of the other eye being examined due to a difference in pupil distances, becomes nearly coincident with the central axis of the light from the measurement system for examination.

The left eye/right eye switching element of the eye refractive power measurement apparatus may be formed, for example, of a pair of right angle prisms. The left eye/right eye switching element can move between a first position, in which light from the measurement system is reflected by the first reflecting surface and is guided toward one of the eyes for examination, and a second position, in which the light from the measurement system is reflected by the second reflecting surface and is guided to the other eye for examination. Consequently, by changing the left eye/right eye switching element between the first and second positions, light from the measurement system can be selectively guided to one eye, and light from the selected eye can be guided to the measurement system.

When the refractive power of the eye under examination is to be measured, it is possible to select the left eye or the right eye as the eye under examination by moving the left eye/right eye switching element over a certain distance and in a certain direction. The eye refractive power measurement apparatus of this invention is capable of sequentially measuring the refractive powers of the left eye and the right eye through a common measurement optical system without moving the entire apparatus.

DESCRIPTION OF THE PREFERRED EMBODIMENT

Figure 1:
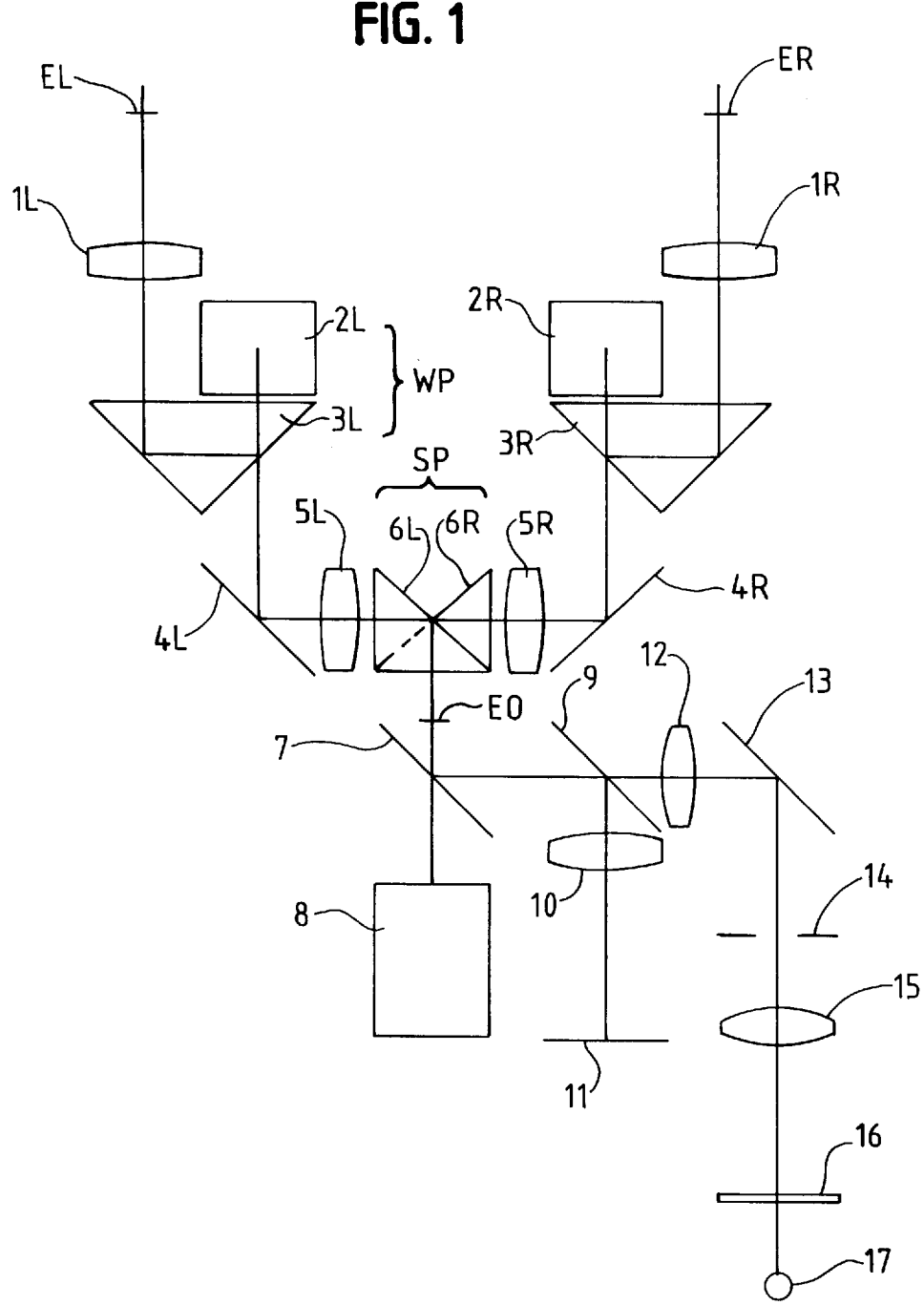
FIG. 1 is a schematic illustration of an eye refractive power measurement apparatus according to one example of this invention.
Figure 2:
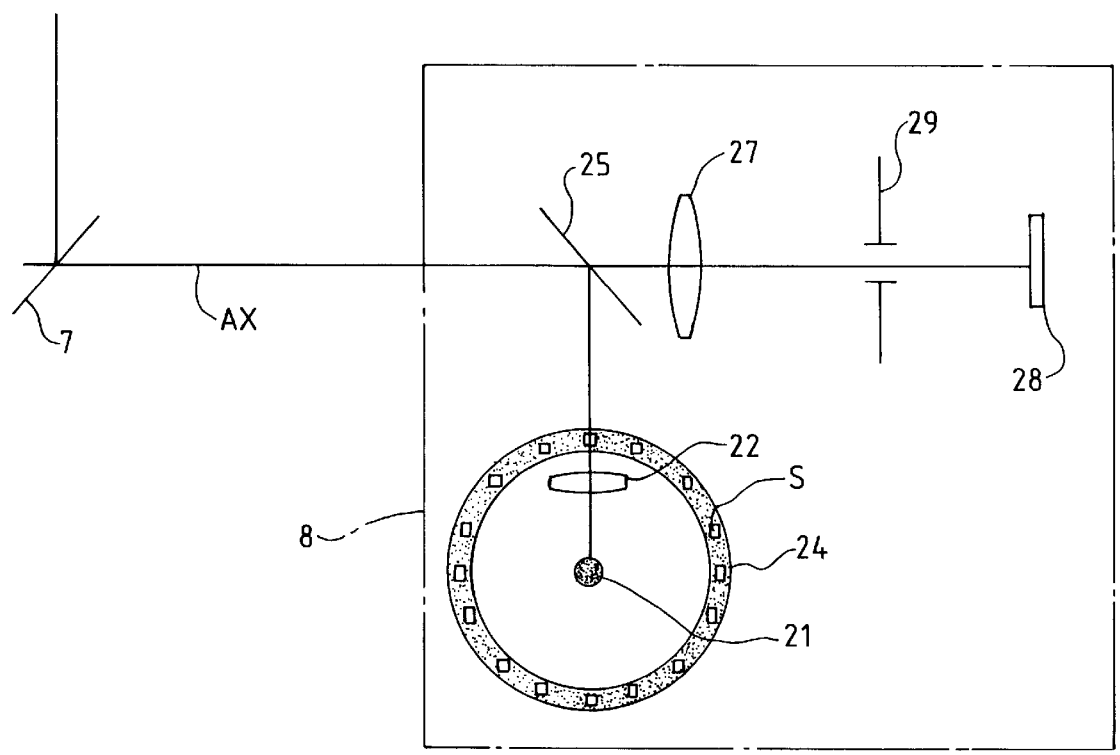
FIG. 2 is a schematic illustration of the internal structure of a refractive power measurement system used in the apparatus shown in FIG. 1.

FIG. 1 shows schematically the construction of one embodiment of the eye refractive power measurement, and FIG. 2 schematically illustrates the internal construction of the eye refractive power measurement system 8 shown in FIG. 1.

The eye refractive power measurement apparatus of this invention has the measurement system 8 mentioned above, an automatic fogging system, and an observing system. The principle employed by the eye refractive power measurement system is referred to as retinoscopy. In this method, an eye refractive power is measured by detecting the speed of movement of a shadow on the pupil. An objective eye refractive power measurement system using one form of retinoscopy is disclosed, for example, by Japanese Laid-open Patent Application No. Sho 55-86437.

The eye refractive power measurement apparatus shown in FIG. 1 includes the eye refractive power measurement system 8 mentioned above for measuring the eye refractive power. FIG. 2 shows the eye refractive power measurement system 8 as including a light-emitting diode 21 that emits infrared (IR) light. This infrared light forms the light source for eye refractive power measurements. The IR light emitted from the light-emitting diode 21 is condensed by a condenser lens 22. The light-emitting diode 21 and the condenser lens 22 are enclosed by a chopper 24 in the form of a hollow cylinder. A number of slit-like openings S are formed in the chopper 24 and extend in a circumferential direction. The openings S are also arranged in the longitudinal direction of the chopper, which is perpendicular to the paper surface in FIG. 2.

The chopper 24 is driven to rotate by a driving unit (not shown in the drawing figures). A linear beam of light transmitted through a slit-like opening S formed in the chopper 24 is incident on a half mirror 25. The half mirror 25 reflects the IR light from light-emitting diode 21 towards the eye under examination. The eye being examined is located on the left in FIG. 2.

The IR light reflected by the half mirror 25 exits from the eye refractive power measurement system 8 and is incident on the half mirror 7.

FIG. 1 shows that the IR light transmitted through the half mirror 7 is incident on the left eye/right eye switching prism SP. This prism includes a pair of right angle prisms 6L and 6R. The IR light incident on the left eye/right eye switching prism SP is reflected, in either the horizontal left direction or the horizontal right direction as shown in FIG. 1, corresponding to the position of the left eye/right eye switching prism SP. When the IR light is incident on the rectangular prism 6L of the left eye/right eye switching prism SP, the light is reflected to the left. When the light is incident on the right angle prism 6R, it is reflected to the right. The IR light reflected to the left by the left eye/right eye switching prism SP goes to the pupil EL of the left eye of the patient. The IR light reflected to the right by the left eye/right eye switching prism SP goes to the pupil ER of the right eye of the patient. The relationship between the positioning of the left eye/right eye switching prism SP and the switching of left eye and right eye examination will be explained later with reference to FIG. 4.

As shown in FIG. 1, the optical system placed between the left eye/right eye switching prism SP and the pupil ER of the right eye has the same construction as that of the optical system placed between the left eye/right eye switching prism SP and the pupil EL of the left eye. Consequently, in FIG. 1, elements forming the optical system placed between the left eye/right eye switching prism and the pupil ER of the right eye are designated by reference characters including the letter R, while elements forming the optical system placed between the left eye/right eye switching prism and the pupil EL of the left eye are designated by reference characters including the letter L. An explanation will now be given with reference to the optical system placed between the left eye/right eye switching prism SP and the pupil EL of the left eye.

The IR light reflected by the right angle prism 6L of the left eye/right eye switching prism SP passes through an optical path having a relay lens 5L and a mirror 4L. The light then enters a pupil distance compensating or adjusting prism WP of the PORRO I type. As is well known, the PORRO I type prism includes a pair of right angle prisms. The pupil distance adjusting prism WP illustrated is made of a pair of right angle prisms 2L and 3L. The function of the pupil distance adjusting prism WP in connection with adjusting the pupil distance will be explained with reference to FIG. 3.

The IR light incident on the right angle prism 2L exits with parallel movement along the direction perpendicular to the paper surface in FIG. 1 and is incident on the right angle prism 3L. The IR light incident on the right angle prism 3L exits with parallel movement along the direction parallel to the paper surface in FIG. 1 and is incident on the relay lens 1L. The IR light is condensed by the relay lens 1L and an image of the light source is formed on the pupil plane of the left eye of the patient. The fundus of the left eye is scanned by the linear beam of light as the chopper 24 is rotated.

The IR light reflected from the left eye of the patient passes through the optical path involving a relay lens 1L, the pupil distance adjusting prism WP, the mirror 4L, the relay lens 5L, and the left eye/right eye switching prism SP. The IR light forms a 1:1 intermediate image of the pupil plane of the left eye of the patient at a position E0. The relay lens 1L and the relay lens 5L, in other words, form a 1:1 relay lens unit with the pupil EL of the left eye and the image position E0 conjugated to each other. The IR light from the 1:1 intermediate image passes through an optical path including the half mirror 7 and the half mirror 25 and enters the objective lens 27. After passing through the objective lens 27, the IR light passes through the stop 29 and forms an image of the pupil of the left eye of the patient on the light-receiving portion 28. The stop 29 has a slit-like opening with its lengthwise direction oriented perpendicularly to the paper surface shown in FIG. 1. This slit-like opening is positioned near the rear-side focal point of the objective lens 27. In this way, it is possible to measure the refractive power of the eye under examination based on the photoelectric output of the light-receiving portion 28 in the known manner.

The eye refractive power measurement apparatus shown in FIG. 1 has an automatic fogging system for relaxing the eye under examination. The automatic fogging system has a visible-light source 17 for illuminating a gazing target 16 with visible light. The visible light from the gazing target 16 passes through a projecting lens 15 and a stop 14. The light is then reflected by the mirror 13 before it is incident on the lens 12. The light from the gazing target 16 then passes through the lens 12, is transmitted through the half mirror 9, and is incident on the half mirror 7. The light reflected by the half mirror 7 passes along the aforementioned optical path and is incident on the right eye pupil ER and the left eye pupil EL of the patient, and is then projected by the lens of the eye under examination onto the retina. In this way, an image of the gazing target 16 is formed on the retina of the eye under examination. The lens 12 is for positioning the stop 14 at a site optically conjugated to the pupil of the eye under examination. Due to the function of the lens 12, even when the eye to be examined is changed, the size of the beam of light incident on the pupil can still be optically kept constant.

If the refractive state of the lens of the eye under examination is constant, then the position of the image of the gazing target 16 formed on the retina of the eye under examination is only a certain single point on the optical axis. A one-to-one correspondence between the position of the image of the gazing target 16 formed on the retina of the eye under examination and the refraction of the lens of the eye under examination is provided. When the eye under examination is allowed to relax, however, it is necessary to form the image of the gazing target at a position slightly in front of the retina so that the eye under examination is oriented at the far point. Consequently, while this point is taken into consideration, the position of the gazing target 16 can be appropriately adjusted. It is possible, therefore, to eliminate the accommodation power of the eye under examination and to allow the eye under examination to relax.

The eye refractive power measurement apparatus shown in FIG. 1 has a system for observing the anterior portion of the eye under examination. In this observing system, the IR light reflected from the eye under examination is incident on the half mirror 7 along a certain optical path. The light reflected by the half mirror 7 is reflected by the half mirror 9 toward the observing system, forming an image of the anterior portion of the eye under examination on an image pickup plane 11 through an image-forming lens 10. Based on the detected image of the anterior portion of the eye under examination, the operator of the apparatus can check to make sure that there is no deviation in position between the eye under examination and the main body of the apparatus and that there are no eyelashes of the patient or other obstructions in the measurement optical path.

The IR light from the eye refractive power measurement system 8 is reflected by the lens surfaces of the relay lenses 1 and 5. This reflected light may become the source of noise when it reaches the light-receiving portion 28. In this case, it is possible to arrange the relay lenses 1 and 5 off-center with respect to the optical axis so that no reflected light reaches the light-receiving portion 28.

Figure 3:
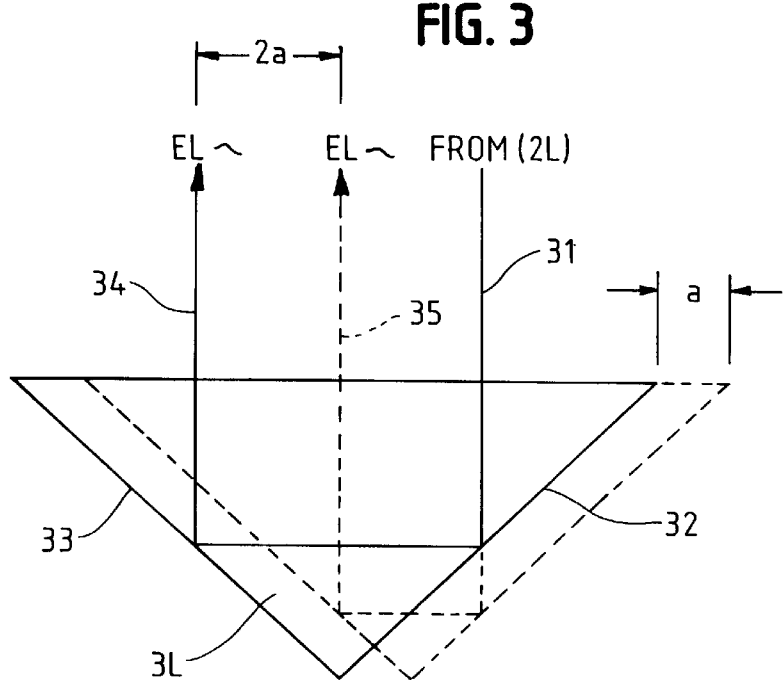
FIG. 3 is an illustration of the pupil distance adjusting function of a pupil distance adjusting prism shown in FIG. 1.

FIG. 3 is a diagram illustrating the pupil distance adjusting function of the pupil distance adjusting prism WP shown in FIG. 1. FIG. 3 shows the optical path through which the light from the right angle prism 2L passes through the right angle prism 3L towards the pupil EL of the left eye.

When the right angle prism 3L is placed at the position indicated by solid lines in FIG. 3, a ray 31 from the right angle prism 2L passes through the optical path represented by a solid line in the figure and is reflected, in order, by a first reflective surface 32 and a second reflective surface 33. The ray then exits as a ray 34. As is shown by the broken lines in the figure, the right angle prism 3L is made to move by a distance a in the horizontal direction, along the plane formed from the incident and exit beams of light, and perpendicular to the incident and exit beams of light. After the ray 31 from the right angle prism 2L is sequentially reflected by the first reflective surface 32 and the second reflective surface 33 along the optical path represented by the broken line in the figure, it becomes the ray 35 and exits. The ray 34 and the ray 35 are parallel to each other and are separated from each other by a distance 2a in the horizontal direction of the figure.

Even when the pupil distance of the patient becomes smaller by 2a and the position of the pupil EL of the left eye is moved by a distance 2a, if the right angle prism 3L is moved by a distance a in the prescribed direction, then it is possible to make the center of the pupil of the left or right eye coincident with the optical axis. By moving the relay lens 1L a distance of 2a and by moving the right angle prism 3L a distance a in the same direction, it is possible to cope with a pupil distance change of 2a.

In this way, in the eye refractive power measurement apparatus shown in FIG. 1, by moving the right angle prism 3L appropriately in the prescribed direction, it is possible to both make the center of the pupil of each eye under examination coincident with the optical axis and adjust the pupil distance. It is also possible to measure the patient's pupil distance based on the movement distance of the right angle prism 3L for adjustment of the pupil distance.

FIG. 4 is a diagram illustrating the left eye/right eye switching function of the left eye/right eye switching prism SP shown in FIG. 1. FIG. 4 is a plan view of the reflective surfaces of the two right angle prisms 6L and 6R forming the left eye/right eye switching prism SP, in the vertical direction, shown in FIG. 1.

Figure 4A:
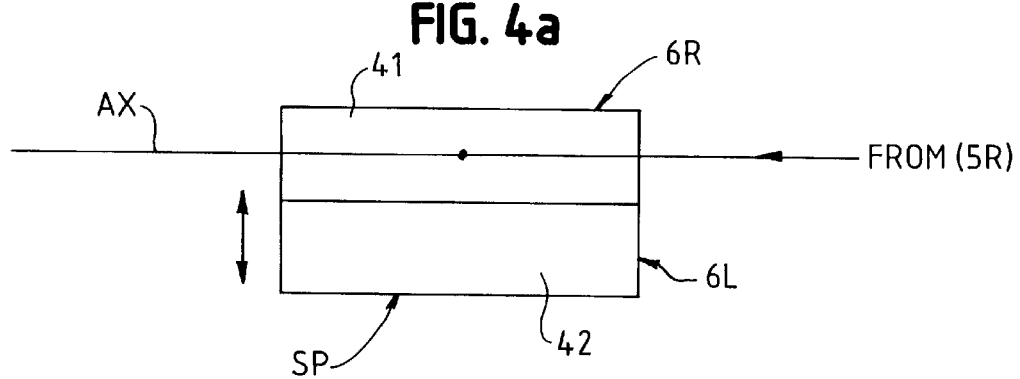
FIG. 4 is an illustration of the left eye/right eye switching function of a left eye/right eye switching prism shown in FIG. 1.

As shown in FIG. 4(a), the left eye/right eye switching prism SP is positioned with respect to the optical axis AX such that the optical axis AX crosses the reflective surface 41 of the right angle prism 6R. In this state, the light from the pupil ER of the right eye, which has been transmitted through the relay lens 5R, is reflected by the reflective surface 41 of the right angle prism 6R. This light is guided through the half mirror 7 to the eye refractive power measurement system and so on. In the state represented in FIG. 4(a), the light from the eye refractive power measurement system passing through the half mirror 7 is reflected by the reflective surface 41 of the right angle prism 6R. The light is guided through the relay lens 5R to pupil ER of the right eye.

Figure 4B:
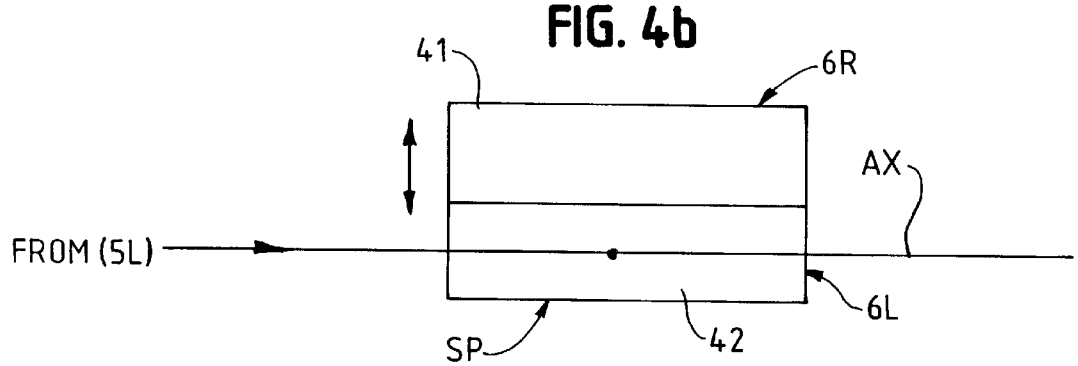

As shown in FIG. 4(b), however, the left eye/right eye switching prism SP is moved over a certain distance in the direction perpendicular to the paper surface as shown in FIG. 1 or, in other words, in the vertical direction on the paper surface shown in FIG. 4. The left eye/right eye switching prism SP is positioned such that the optical axis AX crosses the reflective surface 42 of the right angle prism 6L. In this state, the light from the pupil EL of the left eye passing through the relay lens 5L is reflected by the reflective surface 42 of the right angle prism 6L. The light is guided through the half mirror 7 to the eye refractive power measurement system and so on. In the state shown in FIG. 4(b), the light from the eye refractive power measurement system passing through the half mirror 7 is reflected by the reflective surface 42 of the right angle prism 6L. The light is further guided through the relay lens 5L to the pupil EL of the left eye.

In the eye refractive power measurement apparatus of this invention, after the position deviation between the eye under examination and the main body of the apparatus is checked, the eye under examination is set in a relaxed state by the automatic fogging system. It is then possible to measure the refraction of the eye under examination with the eye refractive power measurement system. Also, when the refractive power of the eye under examination is measured, by moving the left eye/right eye switching prism SP in a certain direction over a certain distance, it is possible to appropriately select the left eye or right eye as the eye to be examined. Consequently, for the eye refractive power measurement apparatus of this invention, it is possible to measure the refractive powers of the left eye and right eye, in order, through a common measurement optical system and without moving the entire apparatus.

In the example of the invention described above, retinoscopy is used in the eye refractive power measurement system. However, retinoscopy is merely one of a number of measurement principles which could be used in the eye refractive power measurement system. Consequently, this invention is not limited to the use of retinoscopy. Other measurement principles may also be adopted.

In addition, in the example of the invention described, the pupil distance adjusting prism WP is of the PORRO I type. However, it is also possible to use a prism of the PORRO II type to form the pupil distance adjusting prism WP.

Finally, in the example of the invention described, prisms are used to perform the left eye/right eye switch and the pupil distance compensation or adjustment. However, it is also possible to use mirrors in place of prisms to realize the left eye/right eye switch and the pupil distance adjustment.

By using a left eye/right eye switch prism, it is possible to select the left eye or right eye appropriately as the eye which is to undergo examination. Consequently, it is possible to measure the refractive powers of the left eye and the right eye through a common optical system and without moving the entire apparatus.

I claim:

1. An apparatus for eye examination, comprising:

measurement means for measuring the refractive power of an eye, including a source of light for projecting a beam of light on a fundus of the eye and a light-receiving element for receiving light reflected from the fundus of the eye and generating a photoelectric output by which the refractive power of the eye under examination is measured; and a switching element for guiding the light from the measurement means to a selected one of the eyes of a patient under examination and for guiding the reflected light from the eye under examination to the measurement system, the switching element including a pair of right angle prisms.

2. The apparatus defined in claim 1, wherein the switching element has a first position and a second position, a first reflecting surface and a second reflecting surface, and is movable between the first position, in which the light from the measurement means is reflected by the first reflecting surface and guided toward one of the eyes under examination, and the second position in which the light from the measurement means is reflected by the second reflecting surface and guided to the other of eyes for examination.

3. The apparatus defined in claim 2, further comprising a pupil distance adjusting element, placed between the switching element and at least one of the eyes of the patient in order to provide alignment of a central axis of the light from the measurement system with the central line of the eye under examination by parallel displacement of the light from the measurement system.

4. The apparatus defined in claim 3, wherein the pupil distance adjusting element includes a right angle prism positioned in a plane formed by an incident beam of light and an exit beam of light and effects the alignment by displacement of the right angle prism in direction perpendicular to the central axis of the light from the measurement system.

5. The apparatus defined in claim 4, wherein the pupil distance of the eyes of the patient is detected based on the parallel displacement of the light by the pupil distance adjusting element.

6. The apparatus defined in claim 3, wherein the pupil distance of the eyes of the patient is detected based on the parallel displacement of the light by the pupil distance adjusting element.

7. The apparatus defined in claim 1, further comprising a pupil distance adjusting element, placed between the switching element and at least one of the eyes of the patient in order to provide alignment of a central axis of the light from the measurement system with the central line of the eye under examination by parallel displacement of the light from the measurement system.

8. The apparatus defined in claim 7, wherein the pupil distance adjusting element includes a right angle prism positioned in a plane formed by an incident beam of light and an exit beam of light and effects the alignment by displacement of the right angle prism in direction perpendicular to the central axis of the light from the measurement system.

9. The apparatus defined in claim 7, wherein the pupil distance of the eyes of the patient is detected based on the parallel displacement of the light by the pupil distance adjusting element.

10. The apparatus defined in claim 8, wherein the pupil distance of the eyes of the patient is detected based on parallel displacement of the light by the pupil distance adjusting element.

11. An apparatus for eye examination, comprising:

measurement means for measuring the refractive power of an eye, including a source of light for projecting a beam of light on a fundus of the eye and a light-receiving element for receiving light reflected from the fundus of the eye and generating a photoelectric output by which the refractive power of the eye under examination is measured;

a switching element for guiding the light from the measurement means to a selected one of the eyes of a patient under examination and for guiding the reflected light from the eye under examination to the measurement system, the switching element including a pair of right angle prisms;

a first optical system for guiding the light from the measurement system positioned between said selected eye and said switching element, and a second optical system disposed between the other of the pair of eyes and said switching element.

12. The apparatus defined in claim 11, wherein the switching element has a first reflecting surface and a second reflecting surface, a first position and a second position, and the switching element is switched from the first position to the second position in order to change said selected eye for examination.

* * * * *